United States Patent [19]

Crosby

[11] Patent Number: 4,698,342

[45] Date of Patent: Oct. 6, 1987

[54] METHOD AND COMPOSITIONS FOR CONTROLLING PAIN, DEPRESSION AND SEDATION

[75] Inventor: Martin G. Crosby, Mt. Pleasant, S.C.

[73] Assignee: Serotonin Industries of Charleston, Charleston, S.C.

[21] Appl. No.: 830,717

[22] Filed: May 20, 1986

Related U.S. Application Data

[60] Division of Ser. No. 755,367, Jul. 16, 1985, Pat. No. 4,596,807, which is a continuation-in-part of Ser. No. 716,190, Mar. 26, 1985, abandoned.

[51] Int. Cl.$^4$ .................... A61K 31/34; A61K 31/40; A61K 31/435; A61K 31/495
[52] U.S. Cl. .................................. 514/253; 514/277; 514/282; 514/419; 514/474
[58] Field of Search .............. 514/277, 282, 253, 419, 514/474

[56] References Cited

PUBLICATIONS

Chem. Abst. (94)–25034t (1981).

*Primary Examiner*—Stanley J. Friedman
*Attorney, Agent, or Firm*—Saidman, Sterne, Kessler & Goldstein

[57] ABSTRACT

Compositions are disclosed for controlling pain, depression, and sedation. The compositions comprise a serotonin precursor such as L-tryptophan or L-5-hydroxytryptophan in combination with a serotonin-specific reuptake inhibitor such as trazodone. In a preferred embodiment, the compositions are coadministered with a narcotic, the composition substantially potentiating the analgesic effect of the narcotic.

9 Claims, No Drawings

METHOD AND COMPOSITIONS FOR CONTROLLING PAIN, DEPRESSION AND SEDATION

CROSS REFERENCE TO RELATED APPLICATIONS

This application is a divisional application of application Ser. No. 755,367, filed July 16, 1985, now U.S. Pat. No. 4,596,807, which is a continuation-in-part of application Ser. No. 716,100, filed Mar. 26, 1985 now abandoned.

BACKGROUND OF THE INVENTION

1. Field of the Invention

This invention relates to medicinal compositions comprising a serotinin precursor such as L-tryptophan and a serotonin-specific reuptake inhibitor such as trazodone. The compositions are useful in controlling pain sedation, and depression in animals. This invention further relates to a method of controlling pain, depression and sedation in animals which comprises administering the medicinal compositions of this invention or components thereof internally. The invention also relates to the method of coadministering the compositions of this invention or components thereof with narcotics to achieve potentiation of the analgesic effect of the narcotic.

2. Description of the Background Art

The use of narcotics is widespread for the control of chronic pain such as that sometimes encountered n advanced disease states of cancer patients. However, long term use of narcotics is met with increasing tolerance in most patients, requiring increased dosages and more frequent administration to achieve a reasonable comfort level. The opiate effects thereof produce a depressant effect with limits dosages and interrupts normal sleep patterns with long term use. Additionally, it frequently becomes impossible to ease the patient's pain to any reasonable degree.

In addition to the opiate effects, it is known that there is a transient increase in brain serotonin levels following administration of a narcotic, e.g., (at an interval of approximately thirty minutes). This increase in brain serotonin levels produced by the administered narcotics produces an analgesic effect. Serotonin is a known calmative neurotransmitter and produces a certain degree of sedation as well.

Serotonin (5-hydroxytryptamine or 5-HT) is present in highest concentration in blood platelets and in the gastrointestinal tract, where it is found in the enterochromaffin cells and the myenteric plexis. Lesser amounts are found in the brain, particularly in the hypothalamus.

Serotonin is found in relatively high concentrations in the lateral gray horns of the spinal cord and in a number of areas in the brain. It can be shown that there is a system of serotonin-containing neurons that have their cell bodies in the raphe nuclei of the brain stem and project to portions of the hypothalamus, the limibic system, the neocortex, and the spinal cord.

Serotonin is formed in the body by hydroxylation and decarboxylation of the essential amino acid L-tryptophan. In the biosynthesis of serotonin from L-tryptophan, L-tryptophan is hydroxylated in the presence of the enzyme tryptophan hydroxylase to form the intermediate product L-5-hydroxytryptophan (L-5-HTP). This intermediate product is decarboxylated in the presence of the enzyme 5-hydroxytryptophan decarboxylase to form serotonin.

After release from serotonergic neurons, much of the released amine is recaptured by an active reuptake mechanism. Additionally, serotonin is inactivated by monoamine oxidase to form 50-hydroxyindoleacetic acid (5-HIAA). 5-HIAA is the principal urinary metabolite of serotonin. For a more complete description of the biosynthesis and metabolism of serotonin, see Gnong, W. F., Review of Medicinal Physiology, pages 190-191 (1979) and Harrison's PRINCIPALS OF INTERNAL MEDICINE, 10th Edition, edited by Petersdorf, R. G. et al., page 827 (1983).

It is also known that ascorbic acid (vitamin C) plays an active role in the hydroxylation of L-tryptophan to L-5-HTP. See CLINICAL GUIDE TO PARENTERAL MICRONUTRITION, Edited by Thomas Baumgartner, Educational Publications, Melrose Park, Ill., page 276 (1984). Further, in the biosynthetic pathway from L-5-HTP to serotonin by decarboxylation of the L-5-HTP, pyridoxine (vitamin B6) plays an integral role. See, CLINICAL GUIDE TO PARENTERAL MICRONUTRITION, Edited by Thomas Baumgartner, Educational Publications, Melrose Park, Ill. page 298 (1984). L-tryptophan or its precursor, L-5-HTP, and pharmaceutically acceptable salts thereof are well known for the treatment of various diseases in animals U.S. Pat. No. 3,795,739 to Birkmayer et al. discloses pharmaceutical compositions for treating Parkinson's disease, said compositions containing L-dopa or a pharmaceutically acceptable salt thereof in mixture with L-tryptophan, L-5-HTP, or pharmaceutically acceptable salts thereof. U.S. Pat. No. 4,161,530 to Coella discloses pharmaceutical compositions useful as hypnotics comprising a pharmacologically active beta receptor-blocking compound and L-tryptophan. U.S. Pat. No. 4,397,866 to Wurtman discloses the administration of L-tryptophan to treat medical conditions where there is a need to sustain or increase brain serotonin levels.

Trazodone, 2-[3-[4-(3-chlorophenyl)-1-piperazinyl]-propyl]-1,2,4-triazolo[4,3-a] pyridin-3(2H)-one) is described in the Merck Index, 9th Edition, 9266 (1976) as a tranquilizer and hypotensive. U.S. Pat. No. 3,381,009 to Palazzo et al. further describes a family of pyridine derivatives including trazodone as having tranquilizing, hypotensive, and analgesic activity.

U.S. Pat. No. 4,444,778 to Coughlin describes a method for improving the arteriosclerotic condition in an animal comprising administering serotonin regulating agents which will reduce the amount of serotonin in the blood vessels, optionally in combination with a tryptophan-poor diet, in order to interfere with the signal for smooth muscle cell proliferation. Among the compounds disclosed for use as a serotonin receptor blocker is trazodone. According to Coughlin, this serotonin receptor blocker operates by inhibiting the proliferation action of serotonin on smooth muscle cells, limiting the ability of platelet-released serotonin to stimulate smooth muscle cell proliferation.

U.S. Pat. No. 4,131,675 to Sylvestrini discloses the use of combinations of L-dopa with trazodone in Parkinsonism in order to avoid the side effects of L-dopa resulting from stimulation of the adrenergic system. Trazodone is further described as having adrenolytic effects.

U.S. Pat. No. 4,329,356 to Holland describes the use of fluoxetine (N-methyl-3-(p-trifluoromethylphenoxyl)-3-phenylpropylamine) in combination with L-5-HTP for the treatment of hypertension. The fluoxetine is described as a specific inhibitor of the serotonin neuron pump, i.e., as a serotonin "uptake" inhibitor.

However, a medicament comprising the combination of a serotonin precursor and trazodone, said medicament useful for the treatment of pain, depression, or as a sedative, is not taught or suggested by the prior art.

SUMMARY OF THE INVENTION

In response to the long-standing need for controlling chronic pain in animals as well as the need for controlling acute pain of short duration, depression, and sedation, the present invention was developed. Recognizing the role played by serotonin in pain management, depression control, and sedation control, the present inventor postulated a mechanism for increasing the brain serotonin levels at the synaptic cleft in an animal. This mechanism, in its first part, comprises the administration of serotonin precursors, optionally with coadministration of the vitamins which act as enzyme cofactors in the biosynthetic pathway for in vivo serotonin production.

However, merely providing serotonin precursor has not proven to be sufficient. An important consideration to the development of the present invention was the further recognition that coadministration of a serotonin-specific reuptake inhibitor would greatly potentiate the effectiveness of enhanced brain serotonin levels, especially where used in conjunction with pain-controlling narcotics.

However, critical to the present invention was the further recognition on the part of the inventor that the reuptake inhibitor must inhibit reuptake of serotonin without also inhibiting reuptake of other neurotransmitters such as norepinephrine, epinephrine, or dopamine. Increasing the activity of norepinephrine, for example, would increase the level of pain in an animal being treated.

Based on the above, the inventor has developed a composition useful as a medicament in the control of chronic pain, acute pain, depression and sedation in animals. Further, the inventor has developed a method for controlling chronic pain, acute pain, depression, and sedation.

The composition of the present invention comprises a serotonin precursor in combination with a serotonin-specific reuptake inhibitor. Optionally, the composition comprising serotonin precursor and seroton-specific reuptake inhibitor further includes at least one of vitamin B6 (pyridoxine) and vitamin C (ascorbic acid), enzymatic cofactors for the biosynthesis of serotonin.

The method of controlling pain, depression, and sedation in animals comprises administering the composition of this invention to an animal. In a preferred embodiment, the composition of this inention is coadministered with a narcotic, thereby greatly enhancing the brain serotonin level increasing effects of the narcotic and potentiating the analgesic effects of the narcotic.

DESCRIPTION OF THE PREFERRED EMBODIMENTS

By the term "serotonin precursor" is intended L-tryptophan, L-5-hydroxytryptophan, pharmacologically equivalent analogues of L-trytophan and L-5-hydroxytryptophan and pharmaceutically acceptable salts of L-tryptophan and L-5-hydroxytryptophan.

L-tryptophan is one of the essential amino acids, not synthesized by the human body. One process for its synthesis is disclosed in U.S. Pat. No. 3,019,232 to Sakurai et al., incorporated by reference herein.

L-5-hydroxytryptophan may be synthesized from 5-benzyloxyindole by Mannich condensation (Ek, W., J. Am. Chem. Soc. 76, 5579 (1954); by catalytic hydrogenolysis of 5-benzyloxytryptophan (Frangatos, C., Can. J. Chem. 37, 1374 (1959)); and by enzymatic hydroxylation of tryptophan (Renson et al., Biochem. Biophys. Res. Commun. 6, 20 (1961)), each incorporated in its entirety herein.

By the term "serotonin-selective reuptake inhibitor" is intended those reuptake inhibitors which have no appreciable effect on other brain aminergic systems. The serotonin-specific reuptake inhibitors of the present invention include, but are not limited to, trazodone and pharmaceutically acceptable salts thereof. Trazodone (currently sold under the trademark "DESYREL," Mead Johnson, Evansville, Ind., and methods for its preparation are described in U.S. Pat. No. 3,381,009 to Pallazzo, incorporated by reference herein.

Other serotonin-specific reuptake inhibitors include, but are not limited to, fluoxetine, described in U.S. Pat. No. 4,018,895, incorporated by reference herein, zimelidine, manufactured by Astra Labs, Westboro, Massachusetts, and citolopram, manufactured by Pfizer Inc., New York, N.Y.

By the term "animal" is intended all animals in which serotonin induces an analgesic effect. Foremost among such animals are humans; however, the invention is not intended to be so limiting, it being within the contemplation of the present invention to treat any and all animals which may experience the beneficial effects of the invention.

By the term "pyridoxine" is intended pyridoxine, natural and synthetic analogues of pyridoxine which are converted by the body to the active form of pyridoxine, and pharmaceutically acceptable salts thereof such as pyridoxine hydrochloride. The synthesis of pyridoxine hydrochloride is described in U.S. Pat. Nos. 2,680,743; 2,734,064; 2,904,551; and 3,024,244, incorporated by reference herein.

By the term "ascorbic acid" is intended ascorbic acid, the synthetic and natural analogues of ascorbic acid which can be converted to the active form in vivo, and the pharmaceutically acceptable salts thereof. A synthetic procedure for producing ascorbic acid is described in U.S. Pat. No. 2,702,808, incorporated by reference herein.

For the present invention, by the term "narcotic" is intended those compounds which achieve analgesia through the mode of enhancement of brain serotonin levels. The term includes, but is not limited to, codeine, oxycodone, propoxyphene, pentazocine, morphine, meperidine, levorphanol, methadone, and the like.

By the term "pharmaceutically acceptable salts" is intended salts with pharmaceutically acceptable acids or bases, e.g., acids such as sulfuric, hydrochloric, nitric, phosphoric acid, etc. or bases such as alkali or alkaline earth metal hydroxides, ammonium hydroxides, alkyl ammonium hydroxides, etc.

By the term "supranormal level" is intended levels of serotonin in excess of those levels normally found as the result of the body's natural production of serotonin or that level induced by the administration of a narcotic alone.

By the term "coadministered" is intended that each of at least two compounds be administered during a time frame wherein the respective periods of pharmacological activity overlap. Thus the term includes sequential as well as coextensive administration of a narcotic and the composition of the present invention.

The compositions of the present invention comprise a serotonin precursor in combination with a serotonin-specific reuptake inhibitor. It is currently estimated that 25-30% of all patients admitted to a hospital demonstrate evidence of at least a certain degree of malnutrition. It is also known that vitamin depletion generally coexists with malnutrition. Accordingly, in a preferred embodiment of the present invention, the compositions of the invention include, in addition to the serotonin precursor and the serotonin-specific reuptake inhibitor, pyridoxine and ascorbic acid or the pharmaceutically acceptable salts thereof. Ascorbic acid is involved in the synthesis of serotonin by facilitating hydroxylation of tryptophan to 5-hydroxytryptopahn. The biosynthetic pathway from 5-hydroxytryptophan to serotonin involves the pyridoxine-catalyzed enzymatic reaction. Thus the addition of at least one of pyridoxine and ascorbic acid to the composition of serotonin precursor and serotonin-specific reuptake inhibitor ensures that a predictable maximum biosynthesis of serotonin will result in all patients regardless of their individual nutritional status.

Typical compositions of the present invention contan, per part by weight of the serotonin-specific reuptake inhibitor or an equivalent amount of the pharmaceutically acceptable salt thereof, 0.5-500 parts by weight of the serotonin precursor or an equivalent amount of the pharmaceutically acceptable salt thereof, and, if present, 0.01-10 parts by weight of pyridoxine or an equivalent amount of a pharmaceutically acceptable salt thereof and 0.1-30 parts by weight of ascorbic acid or an equivalent amount of a pharmaceutically acceptable salt of ascorbic acid.

Preferred compositions contain, per part by weight of the serotonin-specific reuptake inhibitor or an equivalent amount of the pharmaceutically acceptable salt thereof, 0.8-160 parts by weight of the serotonin precursor or an equivalent amount of the pharmaceutically acceptable salt thereof, and, if present, 0.05-4 parts by weight of pyridoxine or an equivalent amount of a pharmaceutically acceptable salt of pyridoxine and 0.4-20 parts by weight of ascorbic acid or an equivalent amount of a pharmaceutically acceptable salt of ascorbic acid.

Typical unit dosage forms contain 25-200 mg of the serotonin-specific reuptake inhibitor or an equivalent amount of the pharmaceutically acceptable salt thereof, 250-4000 mg of the serotonin precursor or an equivalent amount of the pharmaceutically acceptable salt thereof, and, where present, 10-100 mg of pyridoxine or an equivalent amount of the pharmaceutically acceptable salt of pyridoxine, and 50-500 mg of vitamin C or an equivalent amount of the pharmaceutically acceptable salt of vitamin C.

In addition to the pharmacologically active compounds, the new pharmaceutical preparations usually contain suitable excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.1 to 99%, preferably from about 25-85%, of active compound(s), together with the excipient.

The pharmaceutical preparations of the present invention are manufactured in a manner which is in itself known, for example, by means of conventional mixing, granulating, dragee-making, dissolving, or lyophilising processes. Thus, pharmaceutical preparations for oral use can be obtained by combining the active compounds with solid excipients, optionally granulating a resulting mixture and processing the mixture or granules, after adding suitable auxiliaries, if desired or necessary, to give tablets or dragee cores.

Suitable excipients are, in particular, fillers such as sugars, for example lactose or sucrose, mannitol or sorbitol, cellulose preparations and/or calcium phosphates, for example trialcium phosphate or calcium hydrogen phosphate, as well as binders, such as starch, pastes, using, for example, maize starch, wheat starch, rice starch, or potato starch, gelatine, tragacanth, methyl cellulose, hydroxypropylmethyl cellulose, sodium carboxymetyl cellulose, and/or polyvinyl pyrrolidone, and/or, if desired, disintegrating agents, such as the above-mentioned starches, and also carboxymethyl-starch, cross-linked polyvinyl pyrrolidone, agar or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings, which if desired, are resistant to gastric juices and for this purpose, inter alia concentrated sugar solutions, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl cellulose phthalate or hydroxypropylmethyl cellulose phthalate, are used. Dyestuffs or pigments may be added to the tablets or dragee coatings, for example, for identification or in order to characterize different combinations of active compound doses.

Other pharmaceutical preparations which can be used orally are push-fit capsules made of gelatin, as well as soft, sealed capsules made of gelatin and a plasticizer such as glycerol or sobitol. The push-fit capsules can contain the active compounds in the form of granules, for example, mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin or liquid polyethylene glycols, it also being possible to add stabilizers.

Possible pharmaceutical preparations which can be used rectally are, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base; possible base materials are, for example, liquid triglycerides, polyethylene glycols, or paraffin hydrocarbons.

Suitable formulations for parenteral administration are, above all, aqueous solutions of the active compounds in water-soluble form, for example, in the form of water-soluble salts, and also suspensions of the active compounds, such as appropriate oily injection suspensions, for which suitable lipophilic solvents or vehicles, such as fatty oils, for example, sesame oil, or synthetic fatty acid esters, for example, ethyl oleate or triglycerides, are used or aqueous injection suspension which contain substances which increase the viscosity, for example, sodium carboxymethyl cellulose, sorbitol, and/or dextran, and optionally also contain stabilizers.

The compositions of the present invention, in and of themselves, find utility in the control of pain, both mild and severe, be it chronic or acute. Additionally, the compositions of this invention find utility in the treatment of depression and also as a sedative. Serotonin is the natural calmative, mood-regulating neurotransmitter synthesized by the body in vivo. The compounds of the present invention direct the body's own mechanism for dealing with pain, depression, and sedation to its maximum functional potential. In intravenous dosage form, the compositions of the present invention have a sufficiently rapid onset of action to be useful in the management of pain of short duration such as post-surgical pain.

Additionally, a low potency version is useful in the management of mild or chronic pain alone or supplemented by narcotics. This same low potency version is useful in the management of migraines and chronic headaches.

Further, it has also been found that the compositions of the present invention are useful in the management of chronic severe pain such as the pain associated with metastatic disease, neurologic disease such a myofascial pain, and the like.

Coadministration of the compositions of the present invention with narcotics has been found to markedly potentiate narcotic analgesia, while having no attendant respiratory depressant effects. Dosages of narcotics may be substantially reduced and the time interval between doses increased, while still maintaining patient comfort. The combined effect of narcotic and the composition of the present invention yields a combined sedative and antidepressant effect as well which is substantially improved over the use of trazodone or other known antidepressants administered alone.

Further, in the initial phase of pain management according to the present invention, patients previously treated for extended periods with narcotics to control pain experience a significant increase in the amount of dreaming, particularly during the first two weeks of therapy. This increased dreaming indicates that normal sleep patterns are being restored as evidenced by increased REM sleep over previous sleep patterns. Pain management in accordance with the present invention permits patients to undergo all the stages of normal sleep and hence benefit from the restorative properties of sleep. This is to be contrasted with the long term use of narcotics alone which disrupts normal sleep patterns in a manner similar to alcohol intoxication and in which restful and restorative sleep is not achieved. Similarly, benzodiazepines (i.e., Valium ®, Librium ®, Dalmane ®, etc.) actually deplete serotonin from nerve endings which often results in drug-induced depression, additional anxiety, insomnia, and other sleep disturbances.

The effects achieved with the oral administration of the compositions of the present invention are not immediate and, in clinical trials, most patients appear to require five to seven days of treatment to begin responding favorably. At two weeks of therapy, most patients in the clinical trials respond well and near maximal effects are noted at four to six weeks of continued therapy. And, unlike narcotics, uninterrupted long-term therapy is not met with tolerance to the therapy according to the present invention, but rather, even superior results appearing as therapy continues.

The compositions of the present invention may be administered by any means that effects pain management, control of depression, and sedation. For example, administration may be parenterally, subcutaneously, intravenously, intramuscularly, or intraperitoneally. Alternatively, or concurrently, administration can be by the oral route. The dosage administered will be dependent upon the age, health, and weight of the recipient, kind of concurrent treatment, if any, frequency of treatment, and the nature of the effect desired.

Administration of the composition is desirably effected in form 1-4 portions daily, preferably by oral administration, e.g. liquids, capsules, or tablets. Each dosage unit will contain 25-200 mg (100-800 mg per day) of the serotonin-specific reuptake inhibitor, 250-4000 mg (1 g-16 g per day) of the serotonin precursor, 10-100 mg (40 mg-400 mg per day) of the pyridoxine, if present, and 50-500 mg (200-2000 mg per day) of vitamin C, if present.

The following examples are illustrative, but not limitative of the method and composition of the present invention. Other suitable modifications and adaptations of the variety of conditions and parameters normally encountered in clinical therapy and which are obvious to those skilled in the art are within the spirit and scope and this invention.

EXAMPLE 1

The composition of Example 1 contains the following per 30 cc: L-tryptophan 2 grams, pyridoxine 50 mg, and ascorbic acid 250 mg, flavored with cherry syrup and suspended with 2% CMC (sodium carboxy methyl cellulose) as a liquid pharmaceutical carrier.

The composition according to Example 1 when coadministered with trazodone allows for an increase in patient comfort in regard to chronic pain, reduction of narcotic dosage strength and frequency of administration. After one week of therapy, most patients no longer required the use of a sedative-hypnotic for sleep and, after two weeks of continuous therapy, the need for minor tranquilizers was for the most part eliminated.

EXAMPLE 2

This composition contained trazodone powdered tablets, 50 mg, made from commercially obtained Desyrel tablets; L-tryptophan 1 gm, pyridoxine 50 mg, and 250 mg ascorbic acid, flavored with cherry syrup and suspended with 2% CMC. This composition, at 30 cc po qid, delivered 200 mg of trazodone per day and four grams L-tryptophan per day when orally administered and is primarily useful in adjunctive therapy with a narcotic in the management of mild to moderate chronic pain in out-patients who are able to work.

An adequate therapeutic trial of four to six wekks was required for maximal effects to occur.

EXAMPLE 3

The composition of Example 3 contained the following per 30 cc; trazodone 150 mg, L-tryptophan 2 gms, pyridoxine 50 mg, and 250 mg ascorbic acid, flavored with cherry syrup and suspended with 2% CMC.

The medication according to Example 3 was primarily useful when orally administered, in adjunctive therapy with a narcotic in the management of moderate to severe chronic pain in the hospitalized patient and in out-patients who were not engaged in work that involves hazardous tasks. This composition when orally administered is particular useful in helping patients to cope with an overwhelming medical condition such as that which faces terminal cancer patients. There is a definite decrease in both irritability and hostility and a genuine improvement in sleep patterns.

The medication according to Example 3 when orally administered was for use in adjunctive therapy in the management of moderate to severe chronic pain, regardless of etiology, to reduce what is clinically referred to as "agonized suffering." This composition allowed a greater degree of patient comfort with a lower dose of narcotic. Other potential indications included use of this composition alone in the treatment of sleep disturbances, such as insomnia, and the use of this composition alone as an antidepressant.

The dosages of medication according to Examples 2 and 3 was initiated to deliver 50 mg trazodone bid for one day, tid for two days, and then the dose can be increased at a rate of 50 mg per day of trazodone until the maximum total daily dose of trazodone was 600 mg per day or higher (30 cc po qid of Example 3 version).

After two weeks of therapy, successful reductions in the amount of required narcotic was observed. Best results were achieved at four to six weeks of therapy and the gains observed after six weeks were sustained, with continued improvement resulting from long term therapy.

The medications of Examples 1, 2 and 3 were preferably orally administered one hour before meals and at bedtime to increase tryptophan availability to the brain to maximize serotonin formation. Best results were achieved when the product is administered on an empty stomach because L-tryptophan will not be in competition with other LNAA's (large neutral amino acids) for uptake into the brain by carrier transport systems. Altering the diet to a low protein - high carbohydrate - fat meal may also improve response. Iron-deficient patients should be provided with supplemental iron because tryptophan hydroxylase is an iron-containing enzyme required for the synthesis of serotonin.

Some patients may exhibit signs of mental confusion at the onset of therapy, a relatively common occurrence with the use of any antidepressant, particularly in the elderly. Where confusion does occur, lower dosages and more gradual dosage increases are indicated. As with the tricylic antidepressants, the possibility of orthostatic hypotension does exist.

A certain degree of appetite suppression is associated with the use of this composition. This effect may or may not be a desirable consequence of therapy. This medication according to the present invention should not be used in patients with hepatic coma or significant liver disease as these patients already have a supranormal brain serotonin level as s consequence of their disease state.

EXAMPLE 4

A severe myofascial pain patient under the care of a board certified neurologist was hospitalized for nearly three months prior to initiation of the composition of Example 3 (Biogesic HP). There were numerous physician consults and extraordinary injectable narcotic dosages employed (Levodromoran 2 mg injection with Phenergan 25 mg q3h prn pain and Valium 10 mg qid po or im.) and yet the patient remained painful. Plans has already been made to transfer the patient to Emory Pain Control Center prior to initiation of therapy with the composition of Example 3 (Biogesic HP). The patient was started on Biogesic HP at 10 cc tid and displayed a dramatic improvement in pain control and was discharged two days later on Biogesic HP and oral Demerol 50 mg q4-6h prn.

EXAMPLE 5

A terminal cancer patietn under the care of a board certified endocrinologist has such severe unmanageable pain that it could not be controlled even with epidural morphine. Prior to initiation of therapy with Biogesic HP, the patient was receiving injectable Levodromoran 8 mg every three hours around the clock and Brompton's Mixture 30 cc every four hours around the clock. Therapy with Biogesic HP was initiated at 10 ml (50 mg trazodone) twice daily for the first day, three times daily for two days, and then increased at 10 ml daily as tolerated until the maximum total daily dose of trazodone was achieved (i.e., 30 cc po qid). After four weeks of therapy with Biogesic HP at 30 cc qid, the patient required only 4 mg Levodromoran injectio every four hours and 10 cc of Brompton's mixture every eight hours. This previously unmanageable patient has remained on this exact narcotic dosage and schedule for the past eleven months while on Biogesic HP. Numerous consults have remarked that the "patient is more comfortable that I have ever witnessed."

EXAMPLE 6

A terminal cancer patient under the care of a board certified oncologist has such severe pain that he required injectable Levodromoran 2 mg every thirty minutes to one hour around the clock. Biogesic HP was initiated (under the same regimen as in Example 5) and after eight days of therapy the patient required only one to two injections of Levodromonoran 2 mg per eight hour nursing shift to remain comfortable. The patient's improvement in pain control continued up until he quietly expired of disseminated carcinoma involving skin, lymph nodes, bones and lungs.

EXAMPLE 7

A terminal cancer patient under the care of a board certified oncologist had such severe pain that he was always anxious and bitterly hostile. His narcotic requirements were injectable Levodromoran 2 mg-4 mg q3h prn pain at the onset of therapy with Biogesic HP (as in Example 5). A decrease in required narcotics was first observed at ten days of therapy (Levodromoran 2 mg q4-6h prn pain). By then, a genuine taming effect and a favorable personality change was also observed. The patient continued to show improvement in pain control and quietly progressed downhill and expired of disseminated carcinoma involving lungs and bones.

EXAMPLE 8

A terminal cancer patient under the care of a board certified endocrinologist had severe bone pain that would not adequately respond to oral morphine (30 mg po q4h). Biogesic HP was initiated (as in Example 5) and one week later the patient was discharged. The patient has responded favorably and has been controlled at home with Biogesic HP and oral morphine for four months as of 6-7-85.

EXAMPLE 9

A patient with renal cell carcinoma with prior left nephrectomy had a 1-2 year history of lower back pain which was in the lower thoracic spine. She subsequent to the nephractomy was at a later date discovered to have a mass lesion in the T-7 vertebral spine which, although never biopsied, was presumed to be malignant. The mass had developed over a one year period with previous scans showing no mass effect on that occasion. She became paraplegic and remains in the hospital at this time with multiple chronic problems. One of these problems, severe back pain, was very difficult to treat with narcotics including high doses of morphine and Levodromoran. After beginning Biogesic HP (same regimens as in Example 5) the pain medication dose was reduced from Levodromoran 8 mg every 3 hours to approximately 4 mg every 3-4 hours but with marked improvement in pain tolerance. She is not overly sedated and is maintained on this drug regimen at this time.

EXAMPLE 10

A patient with breast carcinoma and diffuse boney metastases experienced a marked increase in diffuse boney pain which was poorly responsive to morphine after initiation of therapy with Nolvadex, an antiestrogen compound. With initiation of treatment with Biogesic HP (same regimen as in Example 5) she was more tolerant of pain although continued to use some morphine.

Having now fully described this invention, it will be appreciated by those skilled in the art that the same can be performed within a wide range of equivalent parameters of composition, conditions, and modes of administration without departing from the spirit or scope of the invention or of any embodiment thereof.

What is claimed as new and desired to be covered by letters patent is:

1. A method for controlling pain, depression, or sedation in an animal comprising co-administering to said animal (1) a composition comprising a serotonin precursor selected from the group consisting of L-tryptophan, L-5-hydroxy tryptophan, and pharmaceutically acceptable salts of L-tryptophan and L-5-hydroxy tryptophan in an amount effective to increase the brain serotonin to a supra normal level, in combination with a serotonin-specific reuptake inhibitor in an amount sufficient to inhibit the reuptake of serotonin, and (2) a narcotic selected from those compounds which achieve analgesia through the mode of enhancement of brain serotonin levels, said narcotic administered in an amount effective to produce analgesia in said animal.

2. The method of claim 1 wherein said composition further includes at least one of pyridoxine, ascorbic acid, or a pharmaceutically acceptable salt of pyridoxine or ascorbic acid in an amount effective to enzymatically cofactor the biosynthesis of serotonin.

3. The method of claim 1 wherein said narcotic is selected from the group consisting of codeine, oxycodone, propoxyphene, pentazocine, morphine, meperidine, levorphanol, and methadone.

4. The method of claim 1 wherein said animal is a human.

5. The method of claim 1 or 2, wherein said serotonin precursor is selected from the group consisting of L-tryptophan, L-5-hydroxytryptophan, and pharmaceutically acceptable salts of L-tryptophan and L-5-hydroxytryptophan and said serotonin-specific reuptake inhibitor is selected from the group consisting of trazodone and pharmaceutically acceptable salts of trazodone.

6. The method of claim 1 wherein said composition comprises per part by weight of said serotoninspecific reuptake inhibitor or an equivalent amount of the pharmaceutically acceptable salt thereof, 0.5-500 parts by weight of said serotonin precursor or an equivalent amount of the pharmaceutically acceptable salt of said serotonin precursor.

7. The method of claim 2 wherein said composition comprises, per part by weight of said serotonin-specific reuptake inhibitor or an equivalent amount of the pharmaceutically acceptable salt of said serotonin-specific reuptake inhibitor, 0.5-500 parts by weight of said serotonin precursor or an equivalent amount of the pharmaceutically acceptable salt of said serotonin precursor, 0.01-10 parts by weight of said pyridoxine or an equivalent amount of the pharmaceutically acceptable salt of said pyridoxine, and 0.1-30 parts by weight of said ascorbic acid or an equivalent amount of the pharmaceutically acceptable salt of said ascorbic acid.

8. The method of claims 1 or 2, wherein said composition is administered to said animal 1-4 times per day, each unit dose containing 25-200 mg of said serotonin-specific reuptake inhibitor or an equivalent amount of the pharmaceutically acceptable salt thereof, 250-4000 mg of said serotonin precursor or an equivalent amount of the pharmaceutically acceptable salt of said serotonin precursor, 10-100 mg of said pyridoxine or an equivalent amount of the pharmaceutically acceptable salt of said pyridoxine, and 50-500 mg of said ascorbic acid or an equivalent amount of the pharmaceutically acceptable salt of said ascorbic acid.

9. The method of claim 8, wherein said composition comprises, per unit dose, 150 mg trazodone, 2 gm L-tryptophan, 50 mg pyridoxine, and 250 mg ascorbic acid and is administered 4 times per day, in combination with an amount of narcotic effective to achieve analgesia.

* * * * *